United States Patent [19]

Stalcup et al.

[11] Patent Number: 5,593,411
[45] Date of Patent: Jan. 14, 1997

[54] ORTHOPAEDIC MILLING GUIDE FOR MILLING INTERSECTING PLANES

[75] Inventors: Gregory C. Stalcup, Columbia City; James C. Harris, Warsaw, both of Ind.

[73] Assignee: Zimmer, Inc., Warsaw, Ind.

[21] Appl. No.: 403,034

[22] Filed: Mar. 13, 1995

[51] Int. Cl.$^6$ .................................................. A61B 17/58
[52] U.S. Cl. .............................. 606/88; 606/87; 606/89
[58] Field of Search ........................... 606/79, 80, 81, 606/82, 83, 84, 85, 86, 87, 88, 89, 96

[56] References Cited

U.S. PATENT DOCUMENTS

| | | | |
|---|---|---|---|
| 4,457,307 | 7/1984 | Stillwell | 128/317 |
| 4,459,985 | 7/1984 | McKay et al. | |
| 4,467,801 | 8/1984 | Whiteside | |
| 4,487,203 | 12/1984 | Androphy | |
| 4,567,885 | 2/1986 | Androphy | |
| 4,574,794 | 3/1986 | Cooke et al. | |
| 4,703,751 | 11/1987 | Pohl | 606/87 |
| 4,721,104 | 1/1988 | Kaufman et al. | |
| 4,722,330 | 2/1988 | Russell et al. | 128/92 |
| 4,759,350 | 7/1988 | Dunn et al. | 128/92 |
| 4,787,383 | 11/1988 | Kenna | |
| 4,892,093 | 1/1990 | Zarnowski et al. | 606/82 |
| 4,926,847 | 5/1990 | Luckman | 606/88 |
| 4,952,213 | 8/1990 | Bowman et al. | 606/79 |
| 4,952,214 | 8/1990 | Comparetto | 606/87 |
| 5,035,699 | 7/1991 | Coates | 606/86 |
| 5,047,032 | 9/1991 | Jellicoe | 606/83 |
| 5,053,037 | 10/1991 | Lackey | 606/79 |
| 5,092,869 | 3/1992 | Waldron | 606/82 |
| 5,098,436 | 3/1992 | Ferrante et al. | 606/88 |
| 5,112,336 | 5/1992 | Krevolin et al. | 606/96 |
| 5,122,144 | 6/1992 | Bert et al. | 606/88 |
| 5,129,907 | 7/1992 | Heldreth et al. | 606/80 |
| 5,129,908 | 7/1992 | Petersen | 606/80 |
| 5,171,244 | 12/1992 | Caspari et al. | 606/88 |
| 5,171,276 | 12/1992 | Caspari et al. | 623/16 |
| 5,176,684 | 1/1993 | Ferrante et al. | 606/86 |
| 5,180,384 | 1/1993 | Mikhail | 606/80 |
| 5,190,547 | 3/1993 | Barber et al. | 606/79 |
| 5,201,768 | 4/1993 | Caspari et al. | 623/20 |
| 5,207,680 | 7/1993 | Dietz et al. | 606/86 |
| 5,207,711 | 5/1993 | Caspari et al. | 623/20 |
| 5,228,459 | 7/1993 | Caspari et al. | 128/898 |
| 5,234,433 | 8/1993 | Bert et al. | 606/88 |
| 5,263,498 | 11/1993 | Caspari et al. | 128/898 |
| 5,304,181 | 4/1994 | Caspari et al. | 606/80 |
| 5,344,423 | 9/1994 | Dietz | 606/87 |
| 5,417,695 | 5/1995 | Axelson, Jr. | 606/89 |
| 5,454,816 | 10/1995 | Ashby | 606/88 |
| 5,474,559 | 12/1995 | Bertin et al. | 606/88 |

FOREIGN PATENT DOCUMENTS

| | | | |
|---|---|---|---|
| 0104732 | 4/1984 | European Pat. Off. | |
| 555003 | 8/1993 | European Pat. Off. | 606/88 |

Primary Examiner—Michael Powell Buiz
Assistant Examiner—Mark S. Leonardo
Attorney, Agent, or Firm—Todd A. Dawson

[57] ABSTRACT

A milling guide for connection to an exposed end of a bone for guiding a milling device along the bone to mill away portions of the bone for accommodation of an orthopaedic implant. The guide includes a plurality of walls positioned in intersecting planes, each of the walls including a slot therein for capturing a milling device. A recess in the travel path of the milling device permits the milling device to rotate from the plane of one wall to that of another wall whereby the milling device is not removed from said milling guide during the cutting of intersecting planes on the bone.

3 Claims, 2 Drawing Sheets

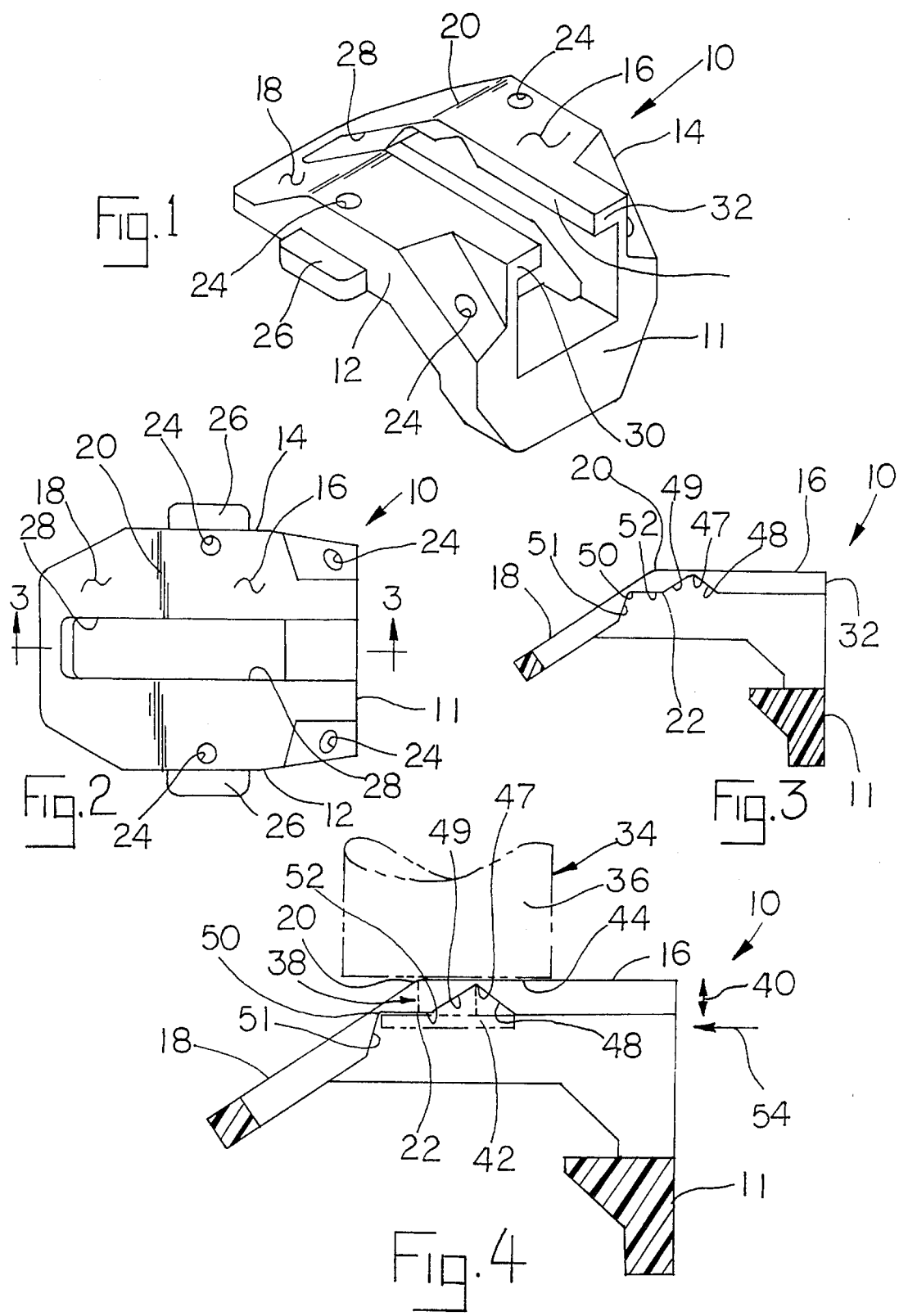

ORTHOPAEDIC MILLING GUIDE FOR MILLING INTERSECTING PLANES

FIELD OF THE INVENTION

The present invention relates to instrumentation used in orthopaedic surgery, and, more particularly, relates to instrumentation used to mill and prepare bone for receiving a prosthesis.

BACKGROUND OF THE INVENTION

In an orthopaedic surgery to replace part or all of a patient's joint with a prosthetic implant, a portion of the implant receiving bone is prepared to closely match the mating surfaces of the implant. During an orthopaedic surgery to replace a knee joint, the distal end of the femur is prepared to accommodate a femoral knee component and the proximal end of the tibia is prepared to accommodate a tibial component.

Prior milling techniques utilized a milling device, normally having a cutter to mill particular areas of bone. Previous guides permitted only lateral-medial axis movement of the milling device. This necessitated various arrangements with a plurality of additional guides to mill or resect portions of the bone into a plurality of intersecting flat surfaces.

The present invention is directed to reduce the number of guides necessary to form intersecting flat surfaces on a bone.

SUMMARY OF THE INVENTION

The milling instrumentation of this invention solves the deficiencies of the prior art systems by providing a milling guide connected to a bone, such as a femur, to allow a surgeon to mill a series of planes or grooves without removing the milling device from the milling guide. A powered milling device having a cutter connected thereto is guided by the slots along the reference planes of the guide to accurately mill away a portion of the bone. The milling device positively engages the slots and associated rails to ensure that the milling device is held substantially perpendicular to the reference planes of the milling guide. Controlling the milling device in this manner ensures an extremely flat milled surface and accurately milled plane intersections and channels for accommodating the implant.

An advantage of the milling guide of the present invention is that it provides a novel milling instrument for preparing a bone surface to accommodate an orthopaedic implant.

Another advantage of the milling guide of the present invention is that it allows an interfit milling device to rotate from one reference plane of milling to another reference plane without release.

Yet another advantage of the milling guide of the present invention is to provide a one piece milling guide capable of guiding a milling device in at least two intersecting reference planes without removal of the device from the guide.

Additional advantages may be understood by a reading of the following description taken with the accompanying drawings.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein:

FIG. 1 is a perspective view of a milling guide according to the present invention which is connectable to a resected femur and guides a milling device for forming intersecting planes on a distal femur;

FIG. 2 is an elevational top view of the milling guide of FIG. 1;

FIG. 3 is a cross sectional view of the milling guide of FIG. 2, taken along the line 3—3 and viewed in the direction of the arrows;

FIGS. 4 and 5 illustrate a milling device captured and guided by the milling guide before and after the milling device rotates to an intersecting plane.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 5:
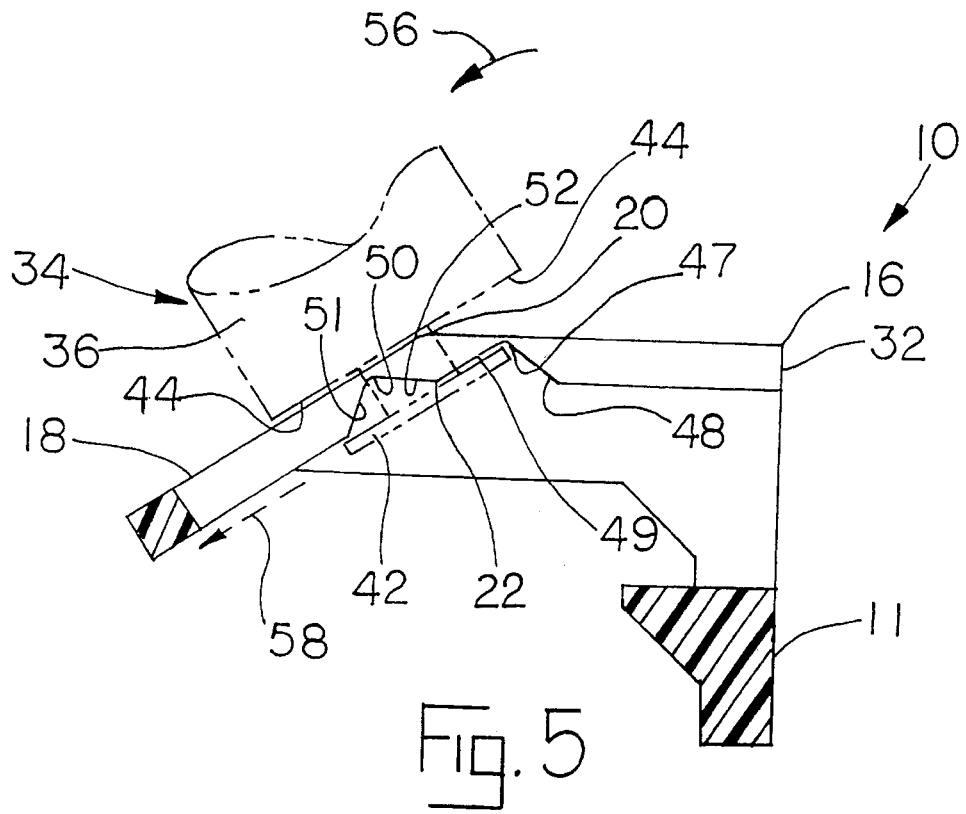

Referring now to FIG. 1, there is shown a perspective view of milling guide 10 of the present invention. Milling guide 10 is formed of metal, preferably stainless steel or another medical grade metal, although other materials may be utilized.

A generally C-shaped milling guide 10 includes a base member 11 having sides 12 and 14 and a plurality of walls 16 and 18 defining a set of reference planes. Walls 16 and 18 intersect at an exterior edge 20 and an interior edge 22. Depending on the particular size and shape of the prosthesis to be attached to the bone, different numbers of milled planes on the bone may be required, thereby requiring different numbers of walls or reference planes on milling guide 10. The present invention is applicable to procedures where two or more reference planes are milled into the bone producing one or more intersecting lines or edges. Additionally the invention may be utilized to form a notch or groove with intersecting bottom walls in a bone, such as a femor or tibia.

As known in the art and more fully described in pending U.S. Pat. Ser. No. 08/169,459, filed Dec. 17, 1993 and hereby explicitly incorporated by reference, milling guides 10 are generally attached to bone by either attaching to a base or directly attaching to the bone by means of pins or screws. Openings 24 in milling guide 10 accommodate and connect with either protuberances on a base attached to a bone or pins set directly into the bone. Milling guide 10 may also include extending tabs 26 for connection to a base.

The intersecting walls 16 and 18, in the embodiment shown in FIG. 1, each includes a slot 28 therethrough that is open or in communication to the slot 28 on an adjacent intersecting wall. As most clearly shown in FIG. 1, slot 28 through wall 16 defines rails 30 and 32 on each side of milling guide 10.

A milling device 34 for use with the milling guide 10 is illustrated in FIGS. 4 and 5, in association with a cross section of guide 10. Milling device 34 includes a drive train (not shown) carried within a generally cylindrical housing 36 that is connected to an external energy source (not shown). As is well known in the industry, the external energy source could be pressurized gas or an electrical power source.

The end of the housing 36 terminates in a bobbin-shaped nose portion 38 as illustrated in FIGS. 4 and 5. The bobbin shape of the nose portion 38 defines a predetermined spacing 40 between the top of a bobbin spacer plate 42 and the end 44 of the housing 36. Shaft 46, including a connected burr 43, is attached to the milling device 34 using a known chuck to securely clamp shaft 46 to device 34. Shaft 46 passes through bobbin shaped nose portion 38. Milling device 34 rotates shaft 46 and burr 43 during operation. Burr 43 may also be referred to as an end cutter and has an end face which is substantially perpendicular to the cutter shaft. It is important to note that the nose portion 38 of milling device 34 is aligned with the guide 10 such that the walls, forming slot 28, are captured between the top of bobbin space plate 42 and end 44 to permit milling device 34 and burr 43 to be guided by the surgeon over the entire length of slot 28.

As mentioned, the bobbin shaped nose portion 38 of milling device 34 engages into slot 28 between, as shown in FIG. 1, rails 30 and 32 to ensure that the milling device and burr 43 are maintained substantially perpendicular to a particular wall of milling guide 10. Maintaining the perpendicular relationship is vital to provide a very flat milled surface to accommodate the implant or alternatively a correctly formed notch or groove depending on the particular need of the prosthesis to be implanted.

The present invention, as most clearly shown in FIG. 3 includes at least one, but preferably two recesses 47 and 50 both formed in the under rails 30 and 32 adjacent slot 28. These recesses adjacent slot 28 create pockets or areas in which bobbin spacer plate 42 may rotate, out of a plane parallel to the plane of the wall in which it is initially, into another plane, one parallel to the plane of the adjacent wall. At all times during movement or sliding of milling device 34, milling device remains captured by milling guide 10. Recesses 47 and 50, in this example, give milling device 34 an additional temporary degree of freedom to move into alignment with the adjacent wall, in this case, wall 18.

As seen in the preferred embodiment of FIGS. 4 and 5, recesses 47 and 50 each are formed of surfaces 48 and 49, and 51 and 52 respectively. Each recess includes a surface that is substantially parallel and co-planar with an opposite adjacent wall. More particularly, surface 52 of recess 50 is co-planar with the bottom of the rails 30 and 32 on wall 16 while surface 49 is co-planar with the bottom of rails 30 and 32 on wall 18. It is this co-planar structure that assists in supporting milling device 34 prior to rotation to a new milling plane. Other mechanisms may be utilized to permit the rotation of milling device 34, but will naturally change the location of the intersection line of the flats milled onto the bone, or alternatively the bottom surfaces of any notches or grooves formed therein.

In operation, a surgeon will attach milling guide 10 to a bone to be milled or resected. The surgeon will then slide milling device 34 into slot 28 so that bobbin shaped nose portion 38 will be captured and slide against rails 30 and 32 on opposite sides of slot 28, as indicated by arrow 54. Milling device 34 will be slid along slot 28 in the plane of first wall 16 until it can go no further. At this location, as depicted in FIG. 4, bobbin spacer plate 42 is within recess 50 adjacent surface 52. The surgeon will now rotate milling device 34 into a new plane as shown in FIG. 5 and indicated by arrow 56.

Figure 6:
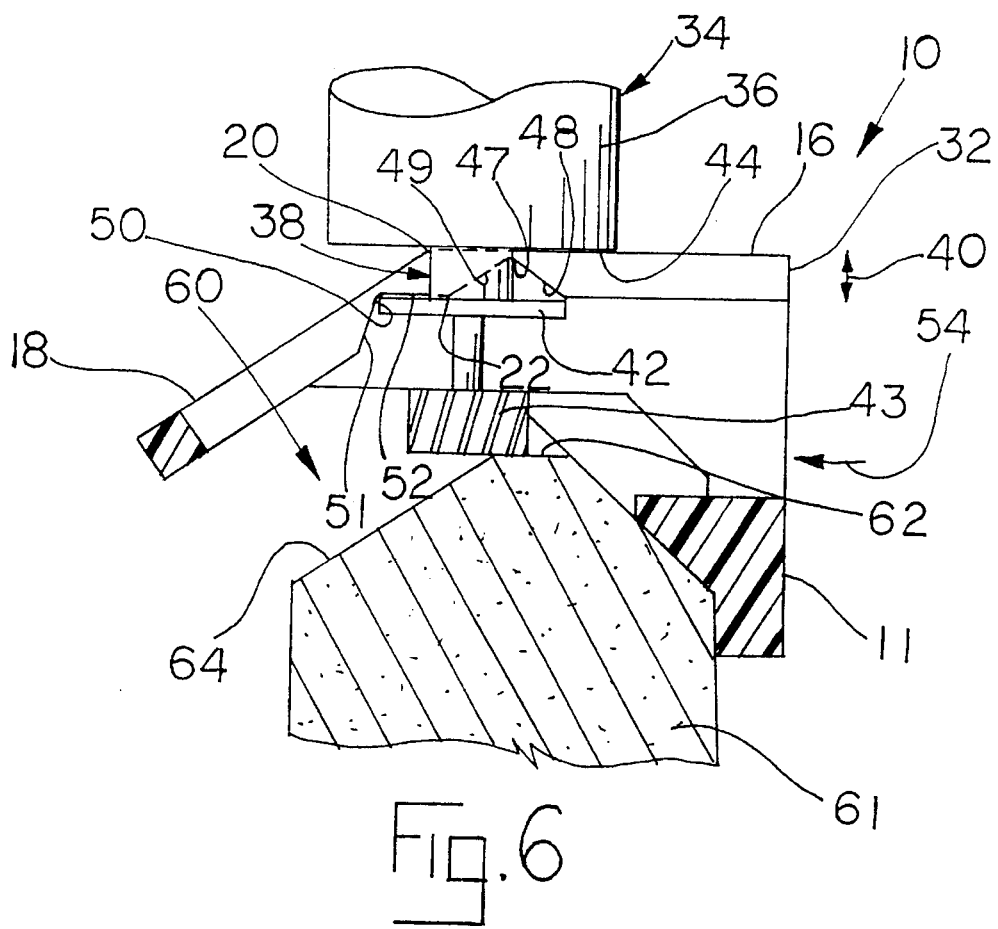
FIG. 6 is a sectional view of one form of the invention, including a burr, disposed on top of a bone.

During this rotation, bobbin spacer plate 42 will move from engagement of surface 52 of recess 50 to that of surface 49 of recess 47. Subsequently, the surgeon will slide milling device 34 along slot 28 in the plane of wall 18, as indicated by arrow 58. The total movement of burr 43 will cause to be milled on the attached bone, a multi-plane cut comprising a flat surface, an intersecting edge and, then another flat surface in a different plane than the first. Milling guide 10 may include a plurality of walls to create a plurality of milled flat surfaces on the attached bone. As shown in FIG. 6, burr 43 is shown having milled a notch or groove 60 into a bone 61, the groove 60 having a first bottom surface 62 parallel to wall 16 and a second bottom wall 64 parallel with wall 18.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. In combination a milling guide and a milling device, said milling device including a bobbin shaped nose portion defined by a plate held in space relationship from a body of the nose by a cylinder, the milling device further including a burr having a shaft, wherein said shaft extends through the cylinder and contacts a drive member to rotate the burr relative to the nose portion, said burr is spaced from the plate by said shaft, said milling guide being adapted for connection to an exposed end of a bone, said milling guide including a first wall and a second wall positioned intersecting planes, each of said first and second walls including a slot therein defined by a pair of rails, said bobbin shaped nose portion being accommodated by said slots such that the plate is on one side of said rails and the body of the nose is on another side of the rails with the cylinder passing between said rails such that said bobbin shaped nose portion is captured by the slot in said walls, the first wall including a notch formed therein adjacent said second wall, said notch accommodating a portion of said plate as said bobbin shaped nose portion moves along the notch in said first wall into the notch in said second wall, said notch constituting means for permitting the milling device to shift from the slot in the first wall into the slot in the second wall without removing the milling device from the milling guide.

2. The combination of claim 1 further including a notch formed in the second wall adjacent the first wall, the notch in the second wall accommodating a portion of the plate as said milling device is shifted from the slot in the second wall into the slot in the first wall.

3. The combination of claim 2 wherein the notch formed in the first wall is in alignment with said one side of said rails forming the slot in said second wall, the notch in the second wall being in alignment with said one side of said rails forming the slot in said first wall.

\* \* \* \* \*